(12) United States Patent
Shepard et al.

(10) Patent No.: US 7,839,974 B2
(45) Date of Patent: Nov. 23, 2010

(54) ARC-SEQUENCING TECHNIQUE FOR INTENSITY MODULATED ARC THERAPY

(75) Inventors: David M. Shepard, Seattle, WA (US); Matthew A. Earl, Crownsville, MD (US); Daliang Cao, Bothell, WA (US)

(73) Assignee: University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 12/412,867

(22) Filed: Mar. 27, 2009

(65) Prior Publication Data
US 2009/0225942 A1 Sep. 10, 2009

Related U.S. Application Data

(63) Continuation of application No. PCT/US2007/079914, filed on Sep. 28, 2007.

(51) Int. Cl.
*A61N 5/10* (2006.01)
(52) U.S. Cl. .......................... 378/65; 378/64
(58) Field of Classification Search .............. 378/64–65
See application file for complete search history.

(56) References Cited

U.S. PATENT DOCUMENTS

2004/0071261 A1 4/2004 Earl et al.
2004/0165696 A1* 8/2004 Lee .............................. 378/65

OTHER PUBLICATIONS

International Preliminary Report on Patentability for application # PCT/US2007/079914 dated Mar. 31, 2009.
International Search Report cited in related PCT application No. PCT/US2007/79914 dated Feb. 29, 2008.

* cited by examiner

*Primary Examiner*—Hoon Song
(74) *Attorney, Agent, or Firm*—Gibb I.P. Law Firm, LLC

(57) ABSTRACT

The invention is directed to a radiation therapy method, and in particular, to a method of conducting an intensity modulated arc therapy (IMAT). The invention provides a planning technique that translates traditional static fixed-field IMRT plans into deliverable IMAT plans and allows IMAT to be realized as a routine clinical delivery technique.

12 Claims, 8 Drawing Sheets

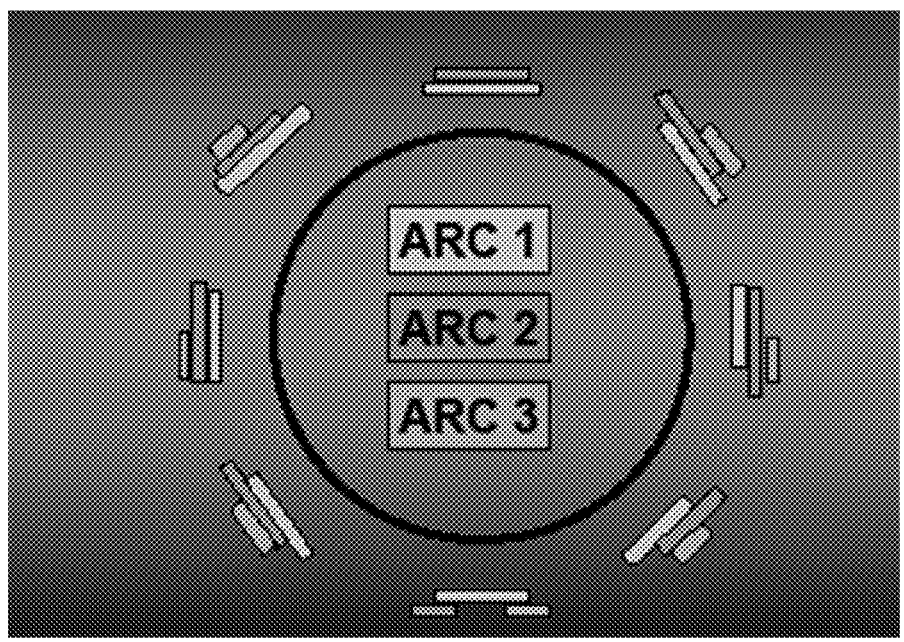
FIG. 4
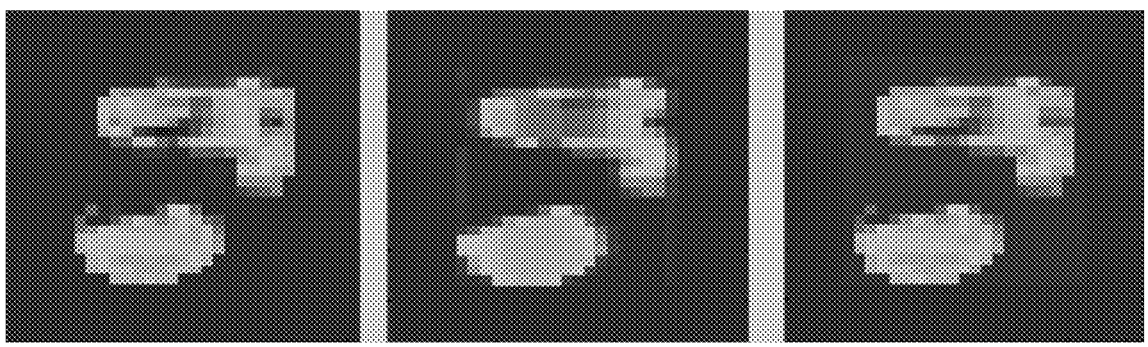
FIG. 5A   FIG. 5B   FIG. 5C

ARC-SEQUENCING TECHNIQUE FOR INTENSITY MODULATED ARC THERAPY

RELATED APPLICATION(S)

This application is a continuation of PCT/US07/79914 filed Sep. 28, 2007, which claims benefit of provisional application Ser. No. 60/848,021, filed Sep. 28, 2006, the entirety of which is incorporated herein by reference.

STATEMENT REGARDING FEDERALLY FUNDED RESEARCH

This invention was made with government support under Grant Number ACI0113045 awarded by the National Science Foundation. The government has certain rights in the invention.

FIELD

The invention relates to radiation therapy, and in particular to a method for the planning and delivery of intensity modulated arc therapy (IMAT).

BACKGROUND

Radiation therapy, in general, is the use of ionizing radiation for the treatment of disease. The most common use is in the treatment of cancer. The goal of radiation therapy for cancer is to destroy any diseased cells while minimizing the damage to healthy tissue. One device for delivering the radiation to a patent is with a linear accelerator, a machine that generates a high-energy beam of radiation that can be controlled and directed onto specified locations.

A recent development in radiation therapy is intensity-modulated radiotherapy (IMRT) in which the intensity of the radiation delivered is modulated within each field delivered. (Webb, "The Physics of Conformal Radiotherapy", Institute of Physics Publishing, Bristol (1997)). The purpose of IMRT is to sculpt the radiation dose distribution so that it maximizes the radiation dose to the tumor while maintaining the radiation dose to normal structures within some pre-specified tolerance. (Webb) In IMRT, highly conformal dose distributions can be achieved through the delivery of optimized non-uniform radiation beam intensities from each beam angle. Successful delivery of IMRT can allow for an escalation of the tumor dose and may enhance local tumor control. The dosimetric advantages of IMRT can also be used to provide a reduced probability of normal tissue complications.

Treatment planning for IMRT is typically performed as a two-step process. First, optimized intensity (fluence) maps are determined for each beam direction. An intensity map indicates the pattern of radiation intensity that should be delivered. Next, a leaf-sequencing algorithm is applied that translates the optimized intensity maps into sets of deliverable aperture shapes. Essentially, the leaf-sequencing converts an "ideal" treatment plan into a plan that can be delivered with a treatment unit, such as a linear accelerator.

Because of the complexity of the treatment plan for IMRT, an automated system is required to determine the intensity maps that produce the optimal radiation dose distribution. Currently available IMRT delivery techniques include fixed field beam delivery (IMRT) and intensity modulated arc therapy (IMAT). When radiation is delivered with fixed beam angles, a series of beam shapes are delivered at each beam angle either dynamically, where the leaves of the MLC move during irradiation, or in a step-and-shoot fashion, where the radiation is paused during the movement of MLC leaves. (Convery and Rosenbloom (1992), Bortfeld et al (1994), Yu, Symons, et al (1995); Boyer A. L., and Yu C. X.; (1999);) In contrast, IMAT uses multiple overlapping arcs of radiation in order to produce intensity modulation. (Yu, C. X. (1995); Yu et al (2002)). IMAT can be produced on a conventional linear accelerator (linac) with a conventional multi-leaf collimator (MLC). During each arc, the leaves of the MLC move continuously as the gantry rotates. Moreover, multiple overlapping arcs are used to modulate the intensity of radiation from each beam direction. Rotational delivery provides the distinct advantage of increased flexibility in shaping the dose distribution and allowing better sparing of adjacent critical structures.

Current inverse-planning algorithms for IMRT use a two-step approach (Boyer and Yu 1999). In the first step, the portal that defines the radiation beam's eye view (BEV) for each radiation beam angle is divided into a set number of finite-sized pencil beams. The radiation dose for each of these pencil beams is then calculated and the corresponding beam intensities are subsequently optimized subject to pre-specified treatment goals. The second step uses the radiation intensity maps from each beam angle and translates the radiation intensity maps into a set of deliverable aperture shapes. During optimization of the radiation intensity, the delivery constraints imposed by the design of various components of the linear accelerator are not taken into account, resulting in treatment plans that are often complex and inefficient to delivery. Beamlet-based Inverse Planning (BBIP) irradiates complex target volumes with a large number of small beams. The number of small beams or beamlets is often more than one thousand. The optimization process adjusts the weights of these beams to produce a desired dose distribution.

The two step approach used by current inverse-planning algorithms is unable to generate treatment plans for IMAT. With IMAT, the radiation is delivered while the gantry rotates continuously. Current leaf-sequencing algorithms fail to take the gantry's continuous movement into account. One feature of IMAT treatment plans is that the aperture shapes for adjacent angles within an arc must not significantly differ. This constraint exists because there are limitations on the speed at which the leaves of the multileaf collimator can travel. This constraint makes it difficult to translate the radiation intensity maps into a set of deliverable arcs.

Thus, it would be desirable to provide an arc-sequencing technique that translates optimized intensity maps into deliverable IMAT arcs which can be used to create treatment plans for IMAT.

SUMMARY

The following presents a summary of some of the disclosure herein. This summary is not an extensive overview, and is intended to neither identify key and/or critical aspects, features and/or elements nor delineate the scope of the claimed subject matter. Its purpose is merely to act as a prelude to the more detailed description that is presented later.

In one embodiment, the invention is directed to method for delivering radiation therapy, comprising creating an intensity modulated radiation therapy (IMRT) plan with static optimized intensity maps; applying a leaf sequencing algorithm to the optimized intensity maps to produce an intensity modulated arc therapy (IMAT) plan, the IMAT plan minimizing discrepancy between the optimized intensity maps and sequenced intensity maps; calculating final doses for the IMAT plan; and delivering the IMAT plan.

In another embodiment, the invention is directed to a method for producing an IMAT plan in an arc sequencer using an algorithm comprising (a) randomly selecting a variable; (b) applying a change to said variable, the size of the change randomly sampled from a Gaussian distribution; (c) accepting or rejecting said change; and repeating steps (a)-(c) until a treatment plan is of acceptable quality.

In a still further embodiment, the invention is directed radiation therapy device, comprising a linear accelerator capable of rotational radiation delivery; a beam shielding device including at least one pair of opposing leaves, said at least one pair defining a track during a treatment segment; and a controller capable of translating a traditional fixed-field IMRT plan into a deliverable IMAT plan following the steps of creating a static beam intensity modulated radiation therapy (IMRT) plan of which the output is optimized intensity maps; producing an intensity modulated arc therapy (IMAT) plan with a specified number of arcs, said IMAT plan minimizing discrepancy between the optimized intensity maps and sequenced intensity maps; calculating final doses for the IMAT plan; and delivering the IMAT plan.

BRIEF DESCRIPTION OF THE FIGURES

FIG. 4 illustrates a rotational IMRT as implemented on a conventional linear accelerator using IMAT.

FIGS. 5A-5C illustrate examples of an optimized intensity map according to the prior art, an ideal intensity map and the intensity map generated by the CIMO sequencer for an IMAT Plan, respectively.

DETAILED DESCRIPTION

Figure 1:
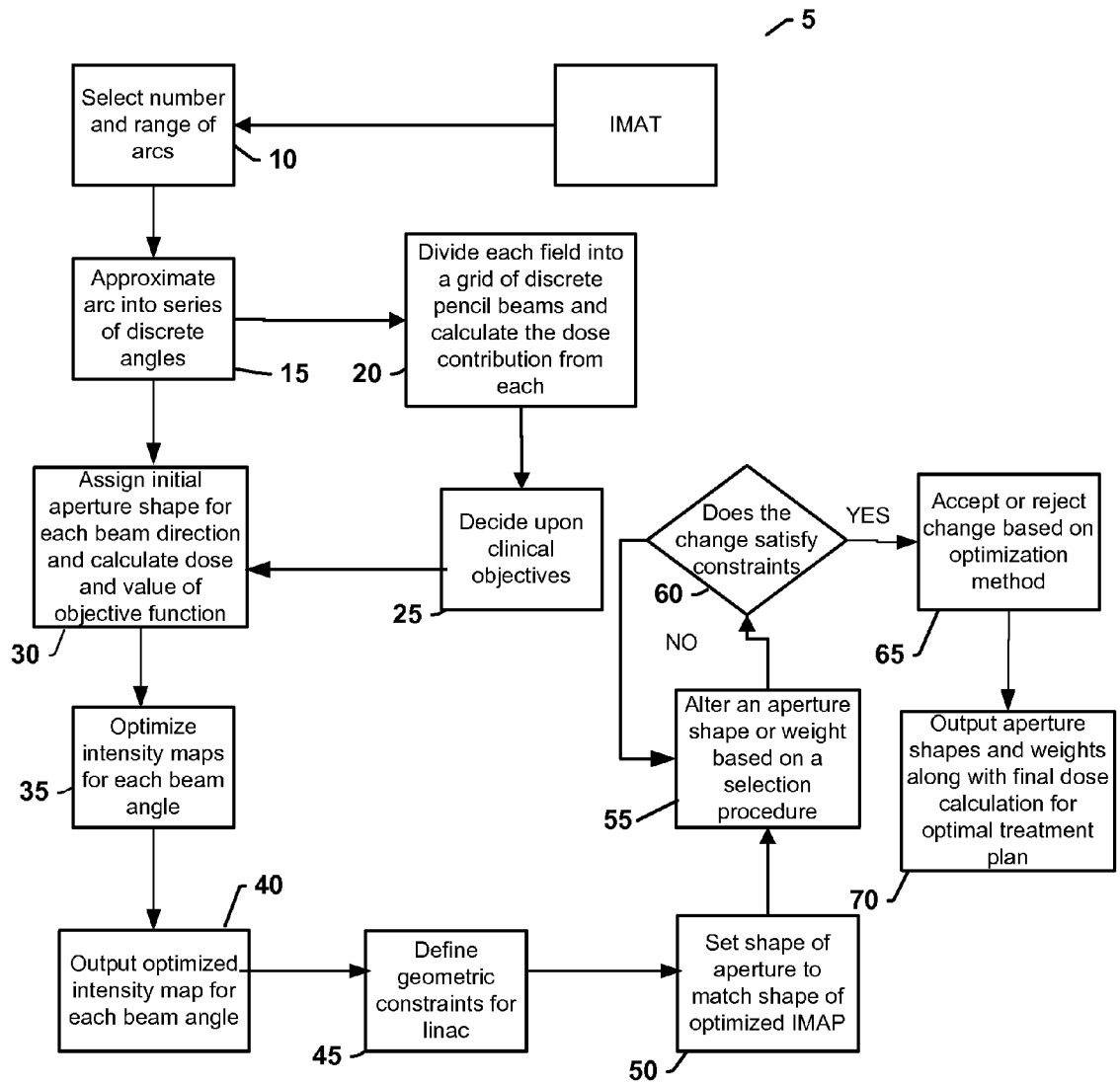
FIG. 1 is a flowchart for continuous intensity map optimization (CIMO).
Figure 2:
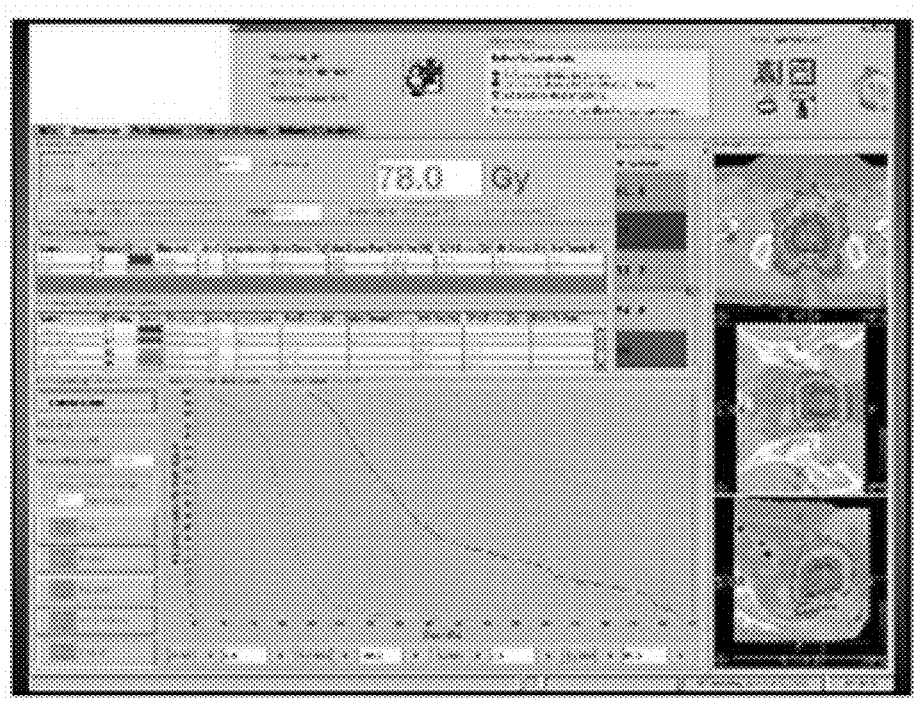
FIGS. 2 and 3 illustrate a Tomotherapy® planning system and a sample plan illustrating the type of dose distribution that is achievable with rotational IMRT according to the prior art.
Figure 3:
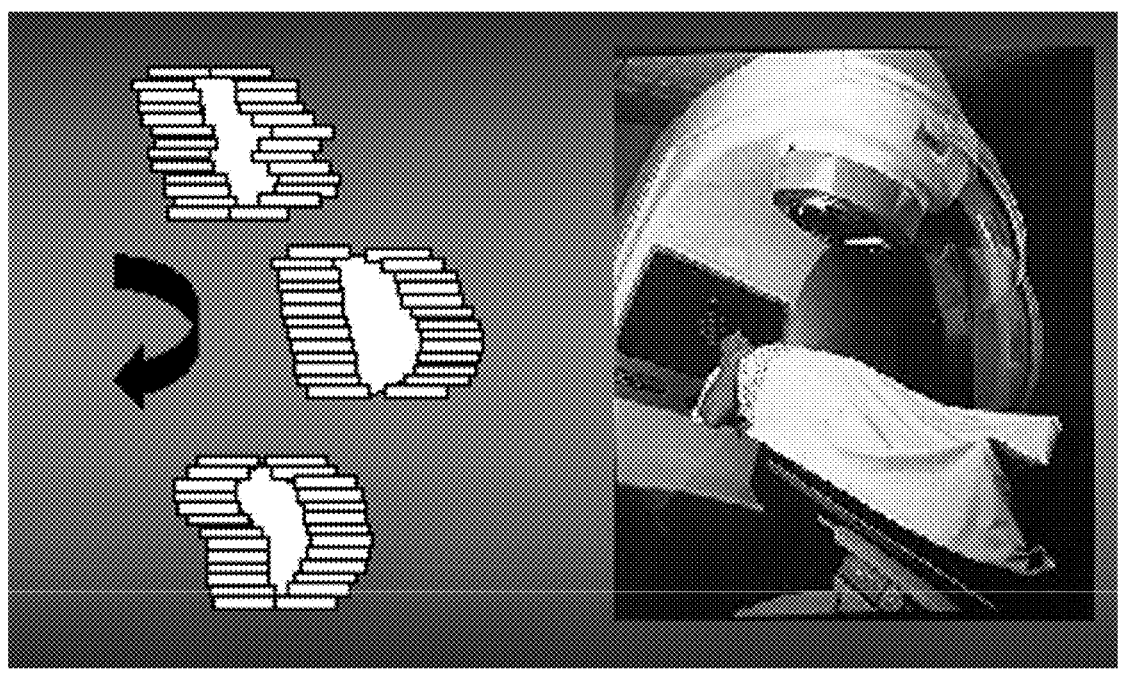

In the following, reference is made to the drawings, wherein like reference numerals are generally utilized to refer to like elements throughout, and wherein the various structures are not necessarily drawn to scale. For purposes of explanation, numerous specific details are set forth in order to provide a more thorough understanding. It may be evident, however, to one skilled in the art that one or more aspects may be practiced with a lesser degree of these specific details. In other instances, well-known structures and devices are shown in block diagram form to facilitate understanding.

A linear accelerator (linac), is a device capable of controlled delivery of radiation to a patient in need of radiation therapy. The radiation exits through the end of the treatment head which is mounted on a gantry. In some linacs, the treatment head is equipped with a multi-leaf collimator (MLC) which shapes the radiation field. A linac has a control unit in a housing. A linac has a gantry which can rotate about a horizontal axis H of rotation around the patient who is lying on the bed. A linac emits a beam of radiation which is aimed at the patient. The beam of radiation can be photons, electrons, or any other type of radiation used for therapy.

During treatment, the radiation beam is directed on a part of the treatment area on the patient. The gantry can rotate about a horizontal axis of rotation; thus allowing for a change in the angle of treatment.

A MLC has multiple thin leafs which can be made of tungsten alloy or other heavy materials stacked in two opposing banks MLC1, MLC2. For one MLC the leaves are usually identical in width, range of travel, and restrictions in relation to the other leaves in the same bank or opposing banks. MLC leaf restrictions can be characterized as static constraints and dynamic constraints. Static constraints can include, but are not limited to, the maximum distance between the most forward position and the most backward position of any leaf in one bank and the minimum distance between opposing leaves in opposing banks. However, it is understood that different MLC's can have widths ranging from 2 mm to 12 mm, range of travel ranging from 1 cm to over 32 cm, and different restrictions. Dynamic constraints include, but are not limited to, the speed of leaf travel, the acceleration and deceleration. These static and dynamic geometric constraints determine the kind of aperture shapes that a particular MLC can form.

Within a linac and in addition to the MLC, a beam shielding device SLD is provided in the path of radiation beam to supplement the MLC in shaping the radiation fields. The beam shielding device includes a plurality of opposing plates. In one embodiment, additional pairs of plates are arranged perpendicular to the opposing plates. The opposing plates move with respect to the plate axis by a drive unit to change the size of the irradiated field. The drive unit includes an electric motor which is coupled to the opposing plates and which is controlled by a motor controller. Position sensors are also coupled to the opposing plates, respectively for sensing their positions. The plate arrangement may alternatively include a multi-leaf collimator (MLC) having many radiation blocking leaves.

In an MLC, there are opposing banks of leaves. Each opposing leaf is attached to a drive unit. The drive units drive the leaves, in and out of the treatment field, thus creating the desired field shape. The MLC leaves, are relatively narrow, and cast a shadow of about 0.5 cm to 1.0 cm onto the treatment area. The position of the leaves of the MLC defines the aperture shape for a treatment.

The intensity of a beam refers to the amount of radiation that accumulates at a specific location of the treatment portal defined by the linac.

A longer radiation exposure time for a specific location in the treatment portal corresponds to a higher radiation intensity. If the MLC opening is fixed during the entire duration of treatment, all locations in the treatment portal would receive approximately the same amount of radiation, and there would be no intensity modulation. A modulated intensity radiation field occurs when the MLC opening changes such that different locations of the treatment portal are exposed for different durations.

The motor controller is part of the Linac Control System (LCS) that also contains a dosimetry system. The dosimetry system measures the output of the radiation beam with a measuring chamber MC and reports to the Linac Control System (LCS) the amount of radiation being delivered at any given time. The LCS coordinates radiation delivery and MLC leaf movement in order to achieve the desired intensity patterns. The LCS controls execution of the prescription generated by the present invention and transferred to the linac control system from the treatment planning system. During delivery, the MLC leaves move in order to achieve the desired treatment.

During treatment planning, a user is allowed to set treatment parameters such as the orientations of beams, ranges of arcs, the number of apertures per beam angle and/or the number of arcs. Using the invention described herein, the planning system automatically optimizes the shape and weightings of the apertures to best meet the objectives of the treatment. The end product of the treatment planning process is a treatment plan that meets the dosimetric requirements specified by the physician. Once a treatment plan is approved by the physician, the treatment planning system will generate a prescription, which specifies the proper coordination between radiation delivery and MLC leaf movements. The prescription, therefore, translates the treatment plan into the computer language understood by the Linac Control System (LCS) and programs the linac for the treatment delivery. In one embodiment, the invention is directed to an arc-sequencing technique that translates optimized intensity maps into deliverable IMAT arcs which can be used to create treatment plans for IMAT. The invention provides a leaf sequencing algorithm referred to as Continuous-Intensity-Map-Optimization (CIMO). The CIMO leaf-sequencing algorithm uses a simulated annealing approach to simultaneously optimize the aperture shapes and weights so as to minimize the sum of absolute differences (SOAD) between the optimized (ideal) and sequenced intensities.

Referring to FIG. 1, there is illustrated a flow chart of the CIMO procedure 5 according to an embodiment of the invention. In a first step 10, the number and range of arcs are selected. After the consideration factors (the number of arcs and range for each arc) are entered, in a step 15, evenly spaced radiation beams are automatically calculated to approximate the range of rotation of the gantry. In a step 20, each field is divided into a grid of discrete pencil beams and the dose distribution for each pencil beam is computed.

In a step 25, the user defines the clinical objectives of the treatment plan. These clinical objects are used to score the quality of the treatment plan throughout the optimization process. The treatment plan quality can be scored by an objective function that quantifies the treatment plan quality into a single numerical value. The objective function can be, by way of example only, a least-square dose difference objected between the desired dose and the achieved dose. The objective function can also be based on dose volume histograms (DVH) or biological based parameters.

At step 30, an initial aperture shape is assigned for each beam angle. For example, the radiation beam's eye view of the target for each beam angle can be used for the starting point, but any aperture shape for each beam angle can be used.

A relative weight (intensity) is assigned to each aperture shape and a radiation dose, radiation dose distribution and dose distribution quality (objective function) are assigned.

An optimized intensity map is then generated for each beam angle at a step 35. Any optimization technique can be utilized to generate the optimized intensity maps, as will be known to those skilled in the art. The optimized intensity maps are then output at a step 40 for each beam angle.

Following creation of intensity maps (IMAPs), the IMAPs are attached to a leaf sequencer and the CIMO leaf-sequencer begins its optimization at step 45. The shape of each aperture is set to match the shape of an optimized intensity map at step 50. The optimizer then progresses through an iterative process to determine the optimal aperture shapes and weights. For each iteration of the optimization, the optimizer randomly selects a variable, with the variables including the multi-leaf collimator (MLC) leaf positions and the aperture weights. For the selected variable, a change of random size is sampled from a probability distribution. For example, a Gaussian distribution can be used.

For changes in an MLC leaf position, the algorithm first determines whether or not the change violates any of the constraints imposed by the multi-leaf collimator at step 60. These constraints are manufacturer-specific and include limitations on interdigitation and requirements on the minimum spacing between opposing leaves. A change in leaf position is accepted or rejected based on the optimization method at step 65. A change in leaf position is automatically rejected if the resulting aperture shape violates any of the MLC constraints. Otherwise, the new SOAD value is computed. A change that results in a lower SOAD is always accepted. However, changes that result in an increased SOAD value are accepted with a probability dictated by an annealing algorithm. Each accepted change is scored as a successful iteration.

As the optimization progresses, the size of the changes in MLC leaf positions and aperture weights are sampled from increasingly narrower Gaussian distributions. In other words, at the beginning of the optimization, large changes are allowed. Only fine-tuning of the parameters occurs towards the end of the optimization. By minimizing the SOAD, the CIMO algorithm minimizes the discrepancies between the optimized and sequenced intensity maps. Optimized aperture shapes and weights are then output at step 70 along with a final dose calculation to create an optimized IMAT plan. FIG. 5 illustrates an example difference between the sequenced and ideal intensity maps.

The CIMO algorithm of the invention serves as the first arc-sequencing tool for intensity modulated arc therapy (IMAT). IMAT is a rotational approach to IMRT delivery. With this approach, the patient is treated with a series of arced beams of radiation. During each arc, the shape of the beam changes continuously as the radiation source rotates around the patient. By overlapping arcs, it is possible to modulate the radiation pattern delivered from each direction. IMAT is able to produce highly conformal radiation dose distribution by combining the dosimetric advantages of rotational delivery with the dose-shaping capabilities of IMRT.

In accordance with the invention, the CIMO algorithm is modified to incorporate IMAT delivery constraints. For rotational delivery, the leaf positions for adjacent angles within an arc are constrained so that the distance of leaf travel does not exceed d where d can be computed using:

$$d = \frac{v_l \Delta \theta}{\omega}$$

Figure 6:
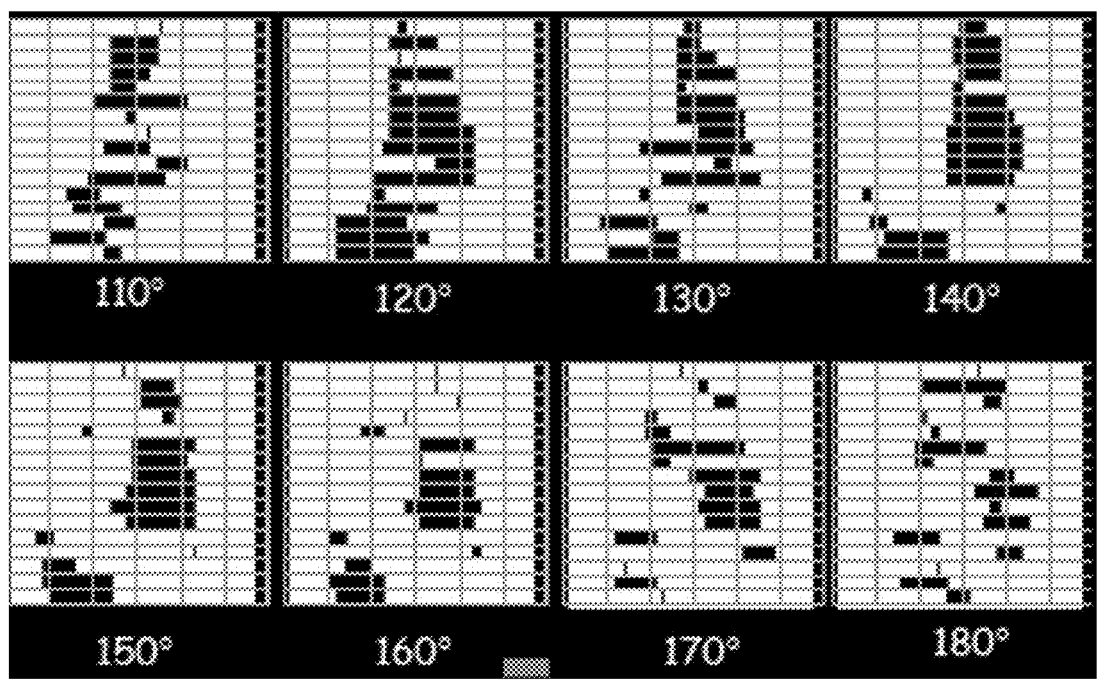
FIG. 6 illustrates a series of aperture shapes for an arc plan generated by a CIMO sequencer. All shapes satisfy the MLC constraints and the IMAT constraints.

Here, $v_l$ is the leaf travel velocity, $\omega$ is the gantry angular rotation speed, and $\Delta\theta$ is the angular separation between adjacent angles, typically 10°. During the arc sequencing, a leaf change is only considered if: (1) the individual aperture is deliverable; and (2) the new aperture shapes do not violate any IMAT delivery constraints. FIG. 6 illustrates a series of aperture shapes (separated by 10 degrees) for an arc created by the CIMO sequencer.

In an embodiment of the invention, a static treatment plan is created with beams separated by 10 degrees. The static optimized intensity maps are input to the CIMO sequencer which produces an IMAT plan. A final dose calculation is then performed using a dose calculation algorithm.

In one embodiment, the beam shielding device comprises a multi-leaf collimator.

As shown in the examples, the CIMO algorithm is a very robust tool for IMAT treatment planning. It rapidly converts optimized treatment plans into plans that can be delivered using the IMAT delivery technique.

Example 1

Figure 7A:
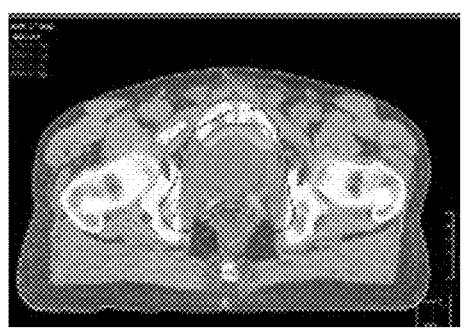
FIG. 7A illustrates an axial view of a 6-arc IMAT treatment plan for a prostate case. The target volume, the bladder, and the rectum are shown. The 90%, 70% and 50% isodose lines are shown on each plot.
Figure 7B:
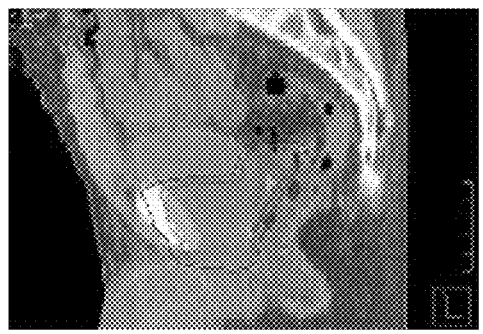
FIG. 7B illustrates a sagittal view of FIG. 7A.

FIGS. 7A and 7B show an axial and sagittal view of a 6-arc IMAT treatment plan for a prostate case. To create this IMAT plan, a 36-field step-and-shoot IMRT plan was created. Next, the optimized intensity maps were exported to the arc-sequencer. The sequencer then determined 6 deliverable arcs that minimized the discrepancy between the optimized and sequenced maps. Finally, a final dose calculation was performed. Note in FIGS. 8A and 8B that a highly conformal plan was produced using 6 arcs. The figures illustrate the target, the bladder, and the rectum. The 90%, 70% and 50% isodose lines are shown on each plot.

Figure 8:
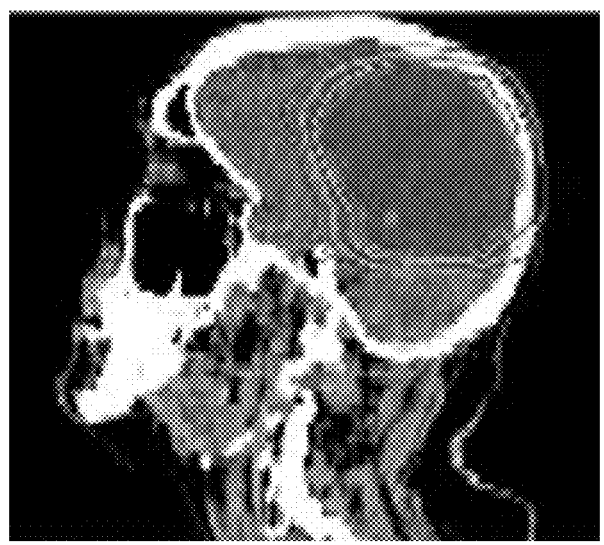
FIG. 8 illustrates a sagittal view of a 4-arc coplanar IMAT plan for a patient with a glioblastoma multiforme. The PTV is shown. The 90%, 70% and 50% isodose lines are shown on each plot.

FIG. 8 shows a sagittal view of a 4-arc (coplanar) IMAT plan for a patient with a glioblastoma multiforme. The 90%, 70% and 50% isodose lines are shown. Using the CIMO arc-based sequencer, a total of 8 IMAT plans were developed. Each plan provides excellent target coverage and a rapid falloff in dose outside of the target. On average, the plans used 4.9 arcs and 532 monitor units. For these results, it was assumed that the dose rate could vary within an individual arc. Additionally, a segment weight optimization was applied to reduce discrepancies between the pre-sequenced and post-sequenced plans. The segment weight optimization does not impact the deliverability of the IMAT plan and is used routinely to improve fixed-field IMRT plan quality after leaf sequencing.

Example 2

Figure 9A:
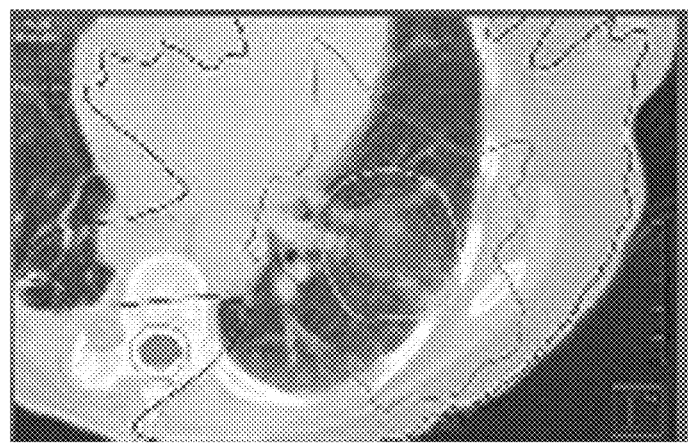
FIG. 9A illustrates a 4-arc IMAT treatment plan in accordance with an embodiment of the invention for a lung patient.
Figure 9B:
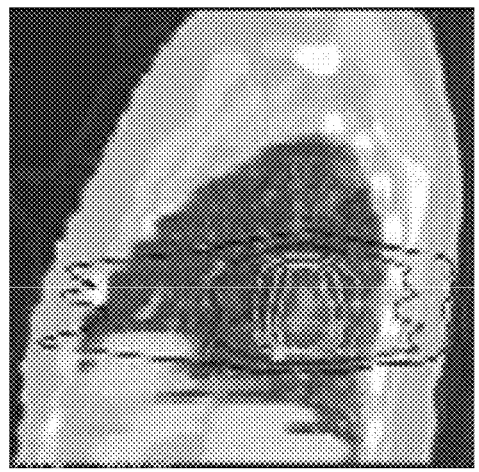
FIG. 9B illustrates an axial slice from the tomotherapy plan of FIG. 9A.
Figure 10:
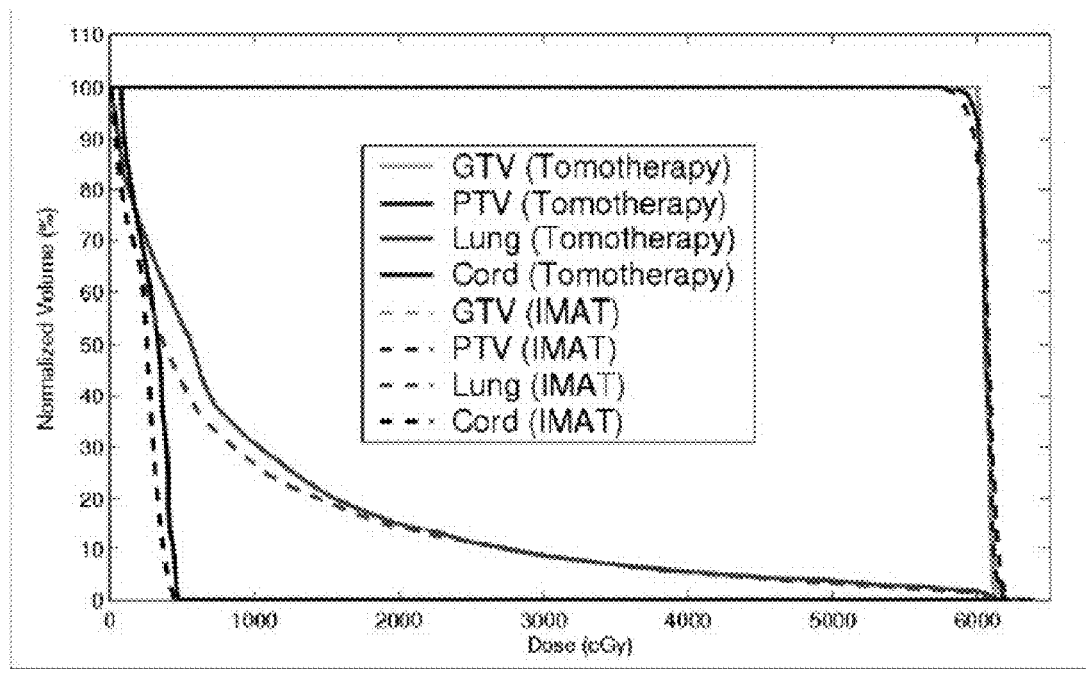
FIG. 10 illustrates a Dose Volume Histogram (DVH) comparison of an IMAT plan (dashed lines) in accordance with an embodiment of the invention and a Tomotherapy® plan (solid lines) for the lung patient shown in FIG. 9.

A comparison of the quality of plans produced by IMAT on a conventional linear accelerator and a Tomotherapy® System is illustrated in FIG. 9A, showing a 4-arc CIMO IMAT treatment plan developed for a lung patient. FIG. 9B shows the corresponding axial slice from the tomotherapy plan. FIG. 10 shows a DVH comparison between the plans in FIG. 10. The IMAT plan provided improved sparing of the lung volumes and the spinal cord with a slight loss in target dose uniformity.

Figure 11:
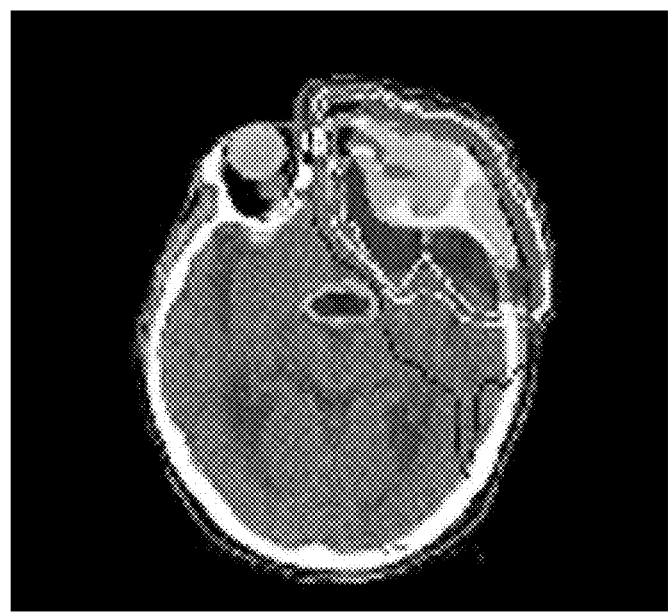
FIG. 11 illustrates an axial slice from an IMAT plan in accordance with an embodiment of the invention for a patient with a tumor of the left orbit.
Figure 12:
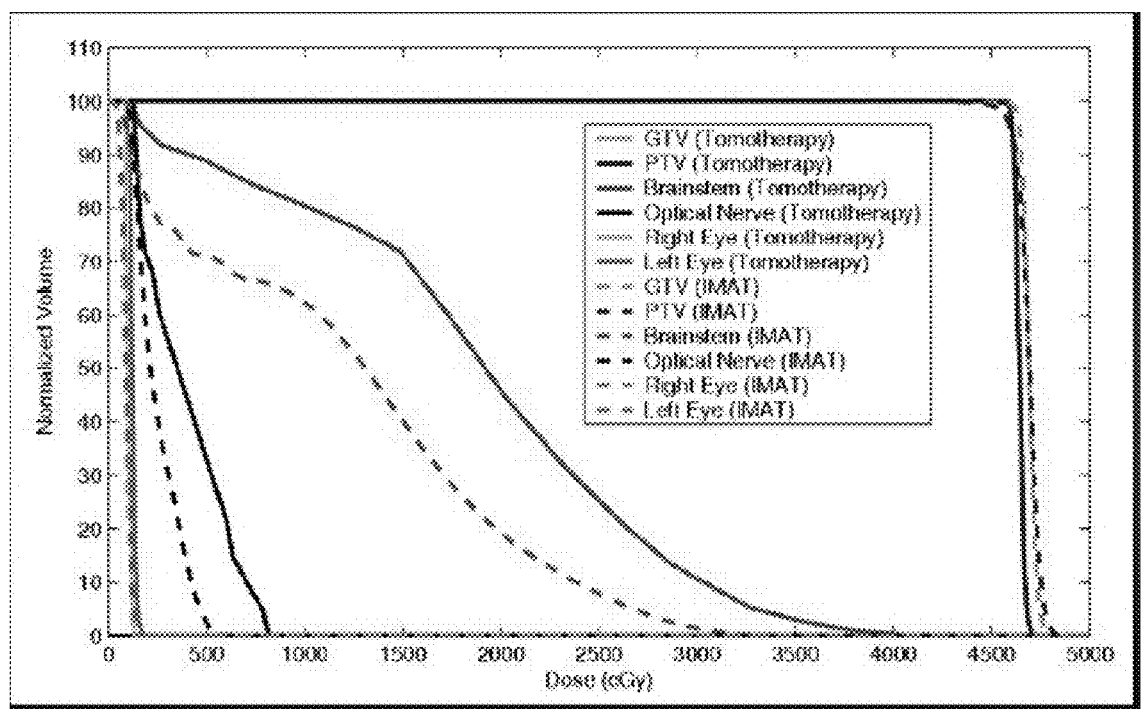
FIG. 12 illustrates the DVH of an IMAT plan (dashed line) in accordance with an embodiment of the invention and a Tomotherapy® plan (solid line) for the orbit case shown in FIG. 11.
Figure 13:
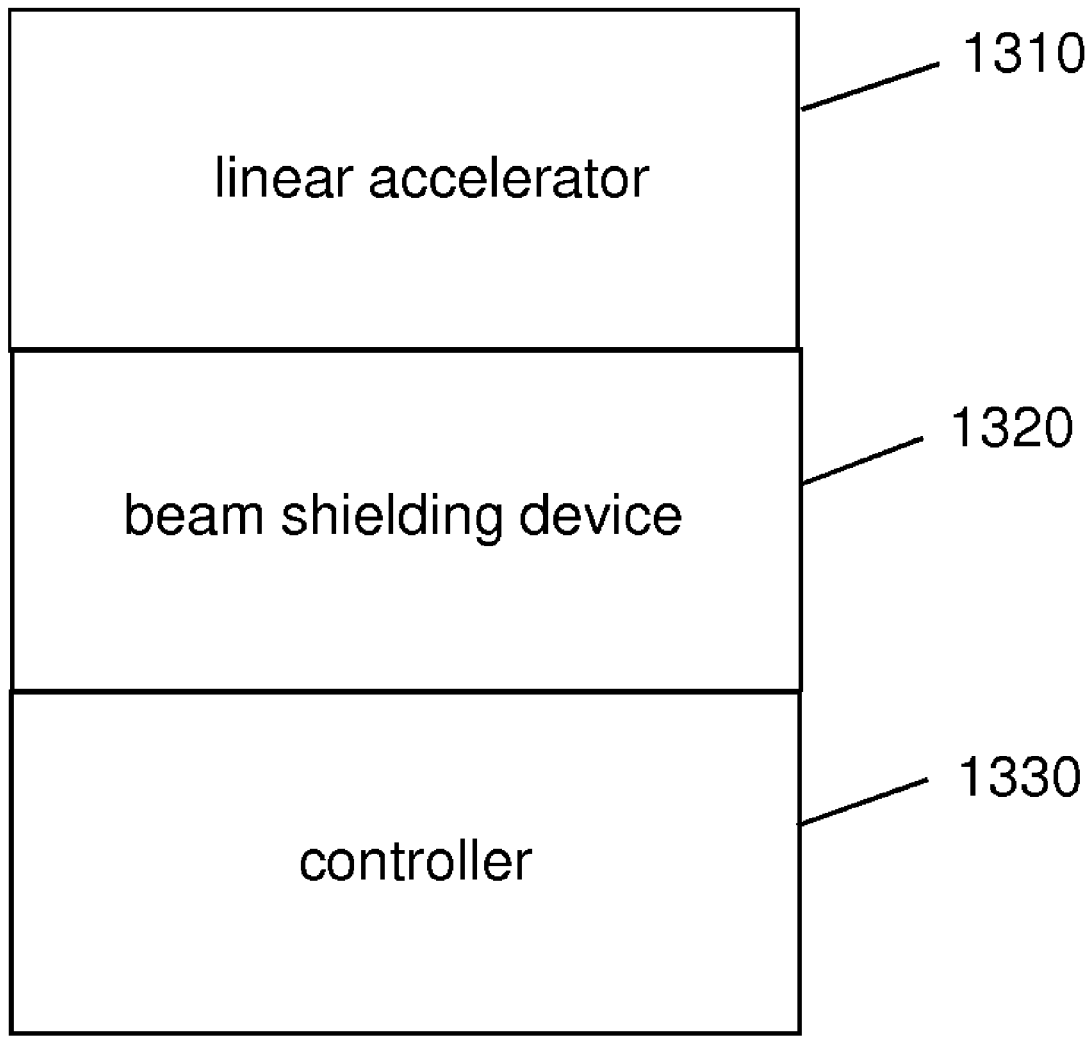
FIG. 13 illustrates a radiation therapy device.

FIG. 11 shows an axial slice from an IMAT plan created with the CIMO algorithm for a patient with a tumor of the left orbit. The IMAT plan used 4 arcs delivered at a couch angle of 90 degrees. FIG. 12 shows a DVH overlay comparing the CIMO IMAT plan with the tomotherapy plan used to treat this patient. The IMAT treatment plan provides a dramatic reduction in dose to the brain stem, optic apparatus, and optic nerve. This reduction in dose to the sensitive structures can be attributed to the preferential angles provided by noncoplanar delivery.

These results demonstrate that IMAT consistently match the quality of plans produced by a Tomotherapy® system while delivering efficient treatments on a conventional linear accelerator. Due to fact that there are fewer than 50 Tomotherapy® units installed in the U.S., IMAT has the potential to greatly expand the number of patients benefiting from the highly conformal dose distributions achievable with arced based IMRT delivery.

FIG. 12 shows a radiation therapy device comprising: a linear accelerator 1310 capable of rotational radiation delivery; a beam shielding device 1320 including at least one pair of opposing leaves, the at least one pair defining a track during a treatment segment; and a controller 1330 capable of translating a traditional fixed-field IMRT plan into a deliverable IMAT plan following the steps of: creating a static beam intensity modulated radiation therapy (IMRT) plan of which the output is optimized intensity maps; producing an intensity modulated arc therapy (IMAT) plan with a specified number of arcs, said IMAT plan minimizing discrepancy between the optimized intensity maps and sequenced intensity maps; calculating final doses for the IMAT plan; and delivering the IMAT plan.

What has been described above includes exemplary aspects and/or implementations. It is, of course, not possible to describe every conceivable combination of components or methodologies, but one of ordinary skill in the art will recognize that many further combinations and permutations are possible. Accordingly, the disclosure herein is intended to embrace all such alterations, modifications and variations that fall within the spirit and scope of the appended claims.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent. In addition, while a particular feature of the disclosure may have been disclosed with respect to only one of several implementations, such feature may be combined with one or more other features of other implementations as may be desired and advantageous for any given or particular application. Furthermore, to the extent that the terms "includes", "having", "has", "with", or variants thereof are used in either the detailed description or the claims, such terms are intended to be inclusive in a manner similar to the term "comprising." Also, "exemplary" as utilized herein merely means an example, rather than the best.

What we claim is:

1. A method for providing a radiation treatment plan in a computer language to a control system, the method comprising:

inputting, to the control system, an intensity modulated radiation therapy (IMRT) plan comprising static optimized intensity maps, wherein:

the IMRT plan comprises a number and range of arcs, each arc corresponds to a beam angle, and each of the static optimized intensity maps corresponds to the beam angle;

inputting, to the control system, geometric constraints for a multi-leaf collimator (MLC);

applying, to the control system, a continuous intensity map optimization (CIMO) leaf sequencing algorithm to each of the static optimized intensity maps, using a simulated annealing approach, to produce an intensity modulated arc therapy (IMAT) plan comprising sequenced intensity maps, wherein the CIMO leaf sequencing algorithm comprises:

initializing an aperture shape of a sequenced intensity map to match that of a corresponding static optimized intensity map;

selecting a random variable for an aperture shape or an aperture weight;

if said random variable satisfies the geometric constraints, then computing a sum of absolute differences (SOAD) between the corresponding static optimized intensity map and the sequenced intensity map using the random variable, and if the computed SOAD is less than a previously computed SOAD, then accepting a change to the sequenced intensity map based on the random variable, otherwise rejecting the change;

repeating, by the control system, the applying of the CIMO leaf sequencing algorithm to each of the static optimized intensity maps to produce an optimized aperture shape and aperture weight for each of the sequenced intensity maps; and outputting, by the control system, the optimized aperture shape and aperture weight for each of the sequenced intensity maps comprising the IMAT plan, and a final dose calculation for the IMAT plan based on the optimized aperture shape and aperture weight for each of the sequenced intensity maps.

2. The method of claim 1, wherein each of the static optimized intensity maps corresponds to a beam angle of 10 degrees.

3. The method of claim 1, wherein the geometric constraints comprise interdigitation and minimum spacing for leaves of the MLC.

4. The method of claim 1, wherein the selecting a random variable for an aperture shape or an aperture weight comprises selecting the random variable from a probability distribution.

5. The method of claim 4, wherein the probability distribution is Gaussian.

6. The method of claim 5, wherein the Gaussian distribution with repeated applications of the CIMO leaf sequencing algorithm is narrowed.

7. A radiation therapy device, comprising:

a linear accelerator capable of rotational radiation delivery;

a beam shielding device including at least one pair of opposing leaves, said at least one pair defining a track during a treatment segment; and a controller configured to translate an intensity modulated radiation therapy (IMRT) plan, comprising static optimized intensity maps, into an intensity modulated arc therapy (IMAT) plan by:

receiving an intensity modulated radiation therapy (IMRT) plan comprising static optimized intensity maps, wherein:

the IMRT plan comprises a number and range of arcs, each arc corresponds to a beam angle, and each of the static optimized intensity maps corresponds to the beam angle;

receiving geometric constraints for a multi-leaf collimator (MLC);

applying a continuous intensity map optimization (CIMO) leaf sequencing algorithm to each of the static optimized intensity maps, using a simulated annealing approach, to produce an intensity modulated arc therapy (IMAT) plan comprising sequenced intensity maps, wherein the CIMO leaf sequencing algorithm comprises:

initializing an aperture shape of a sequenced intensity map to match that of a corresponding static optimized intensity map;

selecting a random variable for an aperture shape or an aperture weight;

if said random variable satisfies the geometric constraints, then computing a sum of absolute differences (SOAD) between the corresponding static optimized intensity map and the sequenced intensity map using the random variable, and if the computed SOAD is less than a previously computed SOAD, then accepting a change to the sequenced intensity map based on the random variable, otherwise rejecting the change;

repeating the applying of the CIMO leaf sequencing algorithm to each of the static optimized intensity maps to produce an optimized aperture shape and aperture weight for each of the sequenced intensity maps; and outputting the optimized aperture shape and aperture weight for each of the sequenced intensity maps comprising the IMAT plan, and a final dose calculation for the IMAT plan based on the optimized aperture shape and aperture weight for each of the sequenced intensity maps.

8. The device of claim 7, the beam shielding device comprising a multi-leaf collimator.

9. The device of claim 7, wherein the geometric constraints comprise interdigitation and minimum spacing for leaves of the MLC.

10. The device of claim 7, wherein the selecting a random variable for an aperture shape or an aperture weight comprises selecting the random variable from a probability distribution.

11. The device of claim 10, wherein the probability distribution is Gaussian.

12. The device of claim 11, wherein the Gaussian distribution with repeated applications of the CIMO leaf sequencing algorithm is narrowed.

* * * * *